United States Patent
Kim et al.

(10) Patent No.: US 9,034,185 B2
(45) Date of Patent: May 19, 2015

(54) SEPARATION OF OLEFINS FROM OLEFINS/PARAFFINS MIXED GAS

(71) Applicants: KOREA INSTITUTE OF ENERGY RESEARCH, Daejeon (KR); SK ENERGY CO., LTD., Seoul (KR)

(72) Inventors: Jong-Nam Kim, Daejeon (KR); Jong-Ho Park, Daejeon (KR); Seong-Jun Lee, Daejeon (KR); Min-Su Ko, Daejeon (KR); Hee Tae Beum, Daejeon (KR); Jongkee Park, Daejeon (KR); Chang Hyun Ko, Daejeon (KR); Sang Sup Han, Daejeon (KR); Soon-Haeng Cho, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 81 days.

(21) Appl. No.: 13/855,957

(22) Filed: Apr. 3, 2013

(65) Prior Publication Data

US 2013/0213793 A1    Aug. 22, 2013

Related U.S. Application Data

(62) Division of application No. 12/593,249, filed as application No. PCT/KR2008/001764 on Mar. 28, 2008, now Pat. No. 8,436,223.

(30) Foreign Application Priority Data

Mar. 29, 2007    (KR) .................... 10-2007-0030970

(51) Int. Cl.
*B01D 15/08* (2006.01)
*C07C 7/12* (2006.01)

(52) U.S. Cl.
CPC ...................................... *C07C 7/12* (2013.01)

(58) Field of Classification Search
None
See application file for complete search history.

(56) References Cited

U.S. PATENT DOCUMENTS 5,026,482 A * 6/1991 Sircar .......................... 210/674
5,365,011 A * 11/1994 Ramachandran et al. .... 585/829

FOREIGN PATENT DOCUMENTS

| CN | 1144793 A | 3/1997 |
| EP | 0708070 A1 | 4/1996 |

(Continued)

OTHER PUBLICATIONS

SIPO Office Action for Chinese Patent Application No. 200880010759.0 which corresponds to the above-identified U.S. application.

(Continued)

*Primary Examiner* — Tam M Nguyen
(74) *Attorney, Agent, or Firm* — LRK Patent Law Firm

(57) ABSTRACT

A method and apparatus for the separation of C4 olefins (butene-1, trans-2-butene, cis-2-butene, etc.) and C4 paraffins (normal butane, isobutane, etc) from a C4 hydrocarbon mixed gas including butene-1, trans-2-butene, cis-2-butene, normal butane, isobutane, etc. is provided. The apparatus includes several adsorption towers loaded with an adsorbent which selectively adsorb olefins and two distillation towers for the separation of the mixture gases of olefins/desorbents and paraffins/desorbents respectively. The basic operating process of the adsorption tower comprises an adsorption step of selectively adsorbing C4 olefin from the feeding mixture, a C4 olefin rinse step of removing a small amount of C4 paraffins adsorbed together with C4 olefins, and a desorption step of desorbing C4 olefins by using a desorbent, and further comprises pressure equalization step, concurrent depressurization step, and accumulation pressure step to increase the yield and concentration of olefins depending on the operation pressure of the adsorption tower.

4 Claims, 2 Drawing Sheets

(56) References Cited

FOREIGN PATENT DOCUMENTS

| | | |
|---|---|---|
| JP | 61-126036 A | 6/1986 |
| JP | 5414664 B2 | 2/2014 |

OTHER PUBLICATIONS

JPO Office Action for Japanese Patent Application No. 2013-191406 which corresponds to the above-identified U.S. application.

* cited by examiner

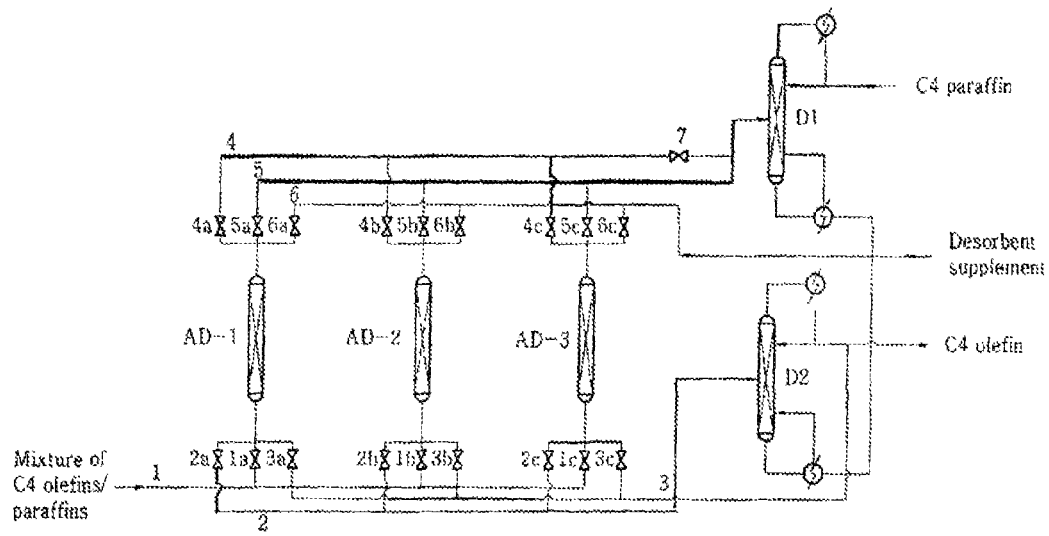

SEPARATION OF OLEFINS FROM OLEFINS/PARAFFINS MIXED GAS

CROSS REFERENCE TO RELATED APPLICATION

This application is a division of U.S. patent application Ser. No. 12/593,249, filed on Sep. 25, 2009, now U.S Pat. No. 8,436,223, the disclosure of which is incorporated by reference in its entirety for all purposes.

BACKGROUND

1. Field

The present invention relates to a method for the separation of C4 olefins (butene-1, trans-2-butene, cis-2-butene, etc.) and C4 paraffins (normal butane, isobutane, etc.) from a C4 hydrocarbon mixed gas including butene-1, trans-2-butene, cis-2-butene, normal butane, isobutane, etc.

2. Description of the Related Art

The known method for the separation of C4 olefins (butene-1, trans-2-butene, cis-2-butene, etc.) and C4 paraffins (normal butane, isobutane, etc.) from a C4 hydrocarbon mixed gas including butene-1, trans-2-butene, cis-2-butene, normal butane, isobutane, etc. involves mainly a distillation process. However, the known method requires the use of distillation towers with a large number of fractionation plates due to the small boiling-point difference of the products to be separated and thus leads to high consumption of energy and to high investment costs.

TABLE 1

Boiling point of the C4 hydrocarbon mixture

| Components | Molecular weight | Boiling point (° C.) |
|---|---|---|
| Isobutane | 58.124 | −11.7 |
| Isobutene | 56.108 | −6.9 |
| Butene-1 | 56.108 | −6.3 |
| 1,3-Butadiene | 54.092 | −4.4 |
| Normal-butane | 58.124 | −0.5 |
| Trans-2-butene | 56.108 | 0.3 |
| Cis-2-butene | 56.108 | 3.7 |

U.S. Pat. No. 4,718,986 (1988) discloses a process for producing butene-1 with a purity of more than 99wt % from the C4 hydrocarbon mixture of butene-1/isobutane/normal butane/butane-2 by using two distillation towers. According to the above patent invention, the C4 mixture is introduced into the first distillation tower to remove isobutane from the top of the tower. The lower stream from the first distillation tower is introduced into the second distillation tower, obtaining butene-1 with a purity of 99 wt % from the top of the second tower and discharging a mixture of normal butane, butene-2 and butene-1from the bottom of the second tower. However, since a considerable amount of butene-1 is discharged with the isobutane stream from the top of the first tower and also with the mixture of normal butane, butene-2 and butene-1 from the bottom of the second tower, the above process results in much loss of butene-1. Accordingly, an adsorptive-separation process which can replace the previous distillation process has been studied.

There are a number of known techniques relating to the adsorption-separation processes for a C4 hydrocarbon mixture, for example, a technique for separating butene-1from a mixture including butene-1/butene-2/isobutylene by using type X or Y zeolite containing potassium ion or barium ion (U.S. Pat. No. 3,723,561, Mar. 27, 1973), a technique for separating butene-1 from a liquid C4 hydrocarbon mixture by using type K-X zeolite (U.S. Pat. No. 4,119,678, Oct. 10, 1978), a technique for separating normal C4 hydrocarbon mixture and isobutylene by using a molecular sieve selective to normal C4 hydrocarbon mixture (U.S. Pat. No. 4,455,445, Jun. 19, 1984), a technique for selectively separating alia olefin alone from olefins having more than 4 carbon atoms by a liquid adsorption process using a zeolite molecular sieve (U.S. Pat. No. 5,132,485, 1992), a pressure-swing adsorption process for the separation of olefins/paraffins having 2-6 carbon atoms in vapor phase by using type 4A zeolite (U.S. Pat. No. 5,365,011, 1994), and a technique for separating paraffins from a mixture of olefins/paraffins having 2-6 carbon atoms in vapor phase using type X or Y zeolite and regenerating the used adsorbents by using desorbents (EP 0708070 B1, 1999). However, there is no adsorptive separation process that can separate C4 olefins with a purify of more than 95 wt % from a mixture of C4 olefins/paraffins, as can be achieved by the present invention.

SUMMARY

The existing vapor adsorption separation process for separating a mixture of olefins/paraffins (ex., EP 0708070 B1, 1999) consists of an adsorption step of introducing the mixture of olefins/paraffins into an adsorption tower to adsorb olefins from the mixture and discharge paraffins, and a desorption step of desorbing the adsorbed olefins by using desorbents.

In the above process, olefins are produced by separation of the mixture of olefins/desorbents resulting from the desorption step via distillation. However, since a small quantity of paraffins is generally adsorbed together with olefins onto olefin selective adsorbents, it is highly difficult to obtain C4 olefins with a high purity of more than 95wt % by a process consisting only of an adsorption step and a desorption step.

In order to separate olefins with high purity, the method of the present invention comprises a sequence of adsorption step—olefin rinse step—desorption step. During the olefin rinse step, a portion of high purity C4 olefins resulting from the distillation of olefins/desorbents (desorption agents) is introduced into the adsorption tower where the adsorption step was completed and thus a small quantity of C4 paraffins adsorbed together with C4 olefins is removed from the adsorption tower so that high purity olefin is obtained at the next desorption step.

The object of the present invention is to provide a method of separating olefins in high yield and purity from a mixture gas of C4 olefins/paraffins, with a reduced consumption of energy, and an apparatus for practicing the method.

The present invention provides a method for separating C4 olefins from a mixture gas composed of C4 olefins/paraffins by performing an adsorption separation process composed of repeated sequential adsorption, olefin rinse and desorption steps in such a way of performing displacement desorption with desorbents, in an apparatus composed of several adsorption towers loaded with adsorbents which adsorb olefins selectively and two distillation towers (one distillation tower for the separation of olefins/desorbents and another distillation tower for the separation of paraffins/desorbents), which comprises the adsorption step for introducing the mixture gas of C4 olefins/paraffins into the adsorption towers loaded with olefin selective adsorbent to adsorb olefins and discharge non-adsorbed paraffins and the desorbents retained in the adsorption tower to the outlet of the adsorption tower; the C4 olefin rinse step to remove a small amount of paraffins adsorbed together with olefins on the adsorbents by introducing a portion of high purity C4 olefins resulting from the distillation process of olefins/desorbents into the adsorption tower after the completion of the adsorption step and thus increasing the purity of olefins; and the desorption step of obtaining C4 olefins by introducing desorbents into the adsorption towers after the completion of the rinse step, wherein said sequential adsorption, olefin rinse and desorption steps are repeatedly performed, wherein each adsorption towers are operated to perform the different steps with each other at the same time point, and wherein the mixture of oiefins/desorbents discharged from the desorption step is introduced into the distillation tower for the separation of olefins/desorbents to obtain high purity olefins by distillation in the distillation tower and the mixture of paraffins/desorbents discharged from the adsorption step is introduced into the distillation tower for the separation of paraffins/desorbents to separating paraffins and desorbents.

Preferably, the method of the present invention further includes a concurrent depressurization step of discharging the paraffin component residue present in the adsorption towers before the olefin rinse step.

Also preferably, the method of the present invention further includes a pressure equalization step at which the paraffin components present in the interior of the adsorption tower after the completion of the adsorption step is transferred to the another adsorption tower which just completed the desorption step by connecting the two adsorption towers so that the pressure of the adsorption towers becomes equalized.

Also preferably, the method of the present invention further includes a concurrent de-pressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

Also preferably, olefin selective adsorbents for use in the method of the present invention is π-complex adsorbent forming π-complex selectively with olefins, type X zeolite or type Y zeolite, and preferably type 13X zeolite.

Also preferably, the adsorbent for use in the method of the present invention is C5 hydrocarbon or C6 hydrocarbon.

Also preferably, in the method of the present invention, the desorbent separated from the olefin/desorbent distillation tower and the paraffin/desorbent distillation tower is recirculated into adsorption tower.

Also preferably, in the method of the present invention, the operating pressure of the adsorption tower in the C4 olefin/paraffin separation process is 1 to 10 atm (absolute pressure) and the temperature is 20 to 150° C.

The present invention also provides an apparatus for the separation of C4 olefins from a mixture gas of C4 olefins/paraffins, by carrying out repeated sequential adsorption, olefin rinse and desorption steps in such a way of performing displacement desorption with the desorbents to separate C4 olefins from the mixture gas, in three adsorption towers AD-1, AD-2 and AD-3 loaded with adsorbents which adsorb olefins selectively and two distillation towers (one distillation tower D2 for the separation of olefins/desorbents and another distillation tower D1 for the separation of paraffins/desorbents), which comprises the adsorption tower AD-1 in which the bottom of the tower is connected with the feeding conduit 1 for the mixture gas of C4 olefins/paraffins through the valve 1a, with the C4 olefin/desorbent discharging conduit 2 through the valve 2a which is connected to the distillation tower D2, and with the conduit 3 through the valve 3a which feeds an amount of C4 olefins produced by the distillation tower D2, and in which the top of the tower is connected with the conduit 4 through the valve 4a which introduces paraffins and desorbents from the olefin rinse step into the distillation tower D1, with the conduit 5 through the valve 5a which feeds paraffins and desorbents discharged from the adsorption step into the distillation tower D1, and with the conduit 6 through the valve 6a which feeds the desorbents into the adsorption tower; the adsorption tower AD-2 in which the bottom of the tower is connected with the feeding conduit 1 for the mixture gas of C4 oiefins/paraffins through the valve 1b, with the C4 olefin/desorbent discharging conduit 2 through the valve 2b which is connected to the distillation tower D2, and with the conduit 3 through the valve 3b which feeds an amount of C4 olefins produced by the distillation tower D2, and in which the top of the tower is connected with the conduit 4 through the valve 4b which introduces paraffins and desorbents from the olefin rinse step into the distillation tower D1, with the conduit 5 through the valve 5b which feeds paraffins and desorbents discharged from the adsorption step into the distillation tower D1, and with the conduit 6 through the valve 6b which feeds the desorbents into the adsorption tower; the adsorption tower AD-3 in which the bottom of (he tower is connected with the feeding conduit 1 for the mixture gas of C4 olefins/paraffins through the valve 1c, with the C4 /desorbent discharging conduit 2 through the valve 2c which is connected to the distillation tower D2, and with the conduit 3 through the valve 3c which feeds an amount of C4 olefins produced by the distillation tower D2, and in which the top of the tower is connected with the conduit 4 through the valve 4c which introduces paraffins and desorbents from the olefin rinse step into the distillation tower D1, with the conduit 5 through the valve 5c which feeds paraffins and desorbents discharged from the adsorption step into the distillation tower D1, and with the conduit 6 through the valve 6c which feeds the desorbents into the adsorption tower; the distillation tower D1 which separates C4 paraffins and desorbents introduced from the adsorption towers AD-1, AD-2 and AD-3; and the distillation tower D2 which separates C4 olefins and desorbents introduced from the adsorption towers AD-1, AD-2 and AD-3.

Preferably, the apparatus of the present invention further includes the valve 7 in the conduit 4 connected to the distillation tower D1.

BRIEF DESCRIPTION OF THE DRAWINGS

FIG. 1 is a schematic view of the apparatus of obtaining high purity olefins from a mixture gas of C4 olefins/paraffins according to the present invention. The apparatus of the present invention comprises three adsorption towers AD-1, AD-2 and AD-3 for separating C4 olefins via selective adsorption and two distillation towers D1 and D2 for separating C4 olefins/desorbents and C4 paraffins/desorbents respectively.

FIG. 2 is a table showing a cycle sequence of the process consisting of seven steps.

FIG. 3 is a fable showing a cycle sequence of the process composed of four steps.

FIG. 4 is a table showing a cycle sequence of the process composed of three steps.

DETAILED DESCRIPTION

Figure 5:
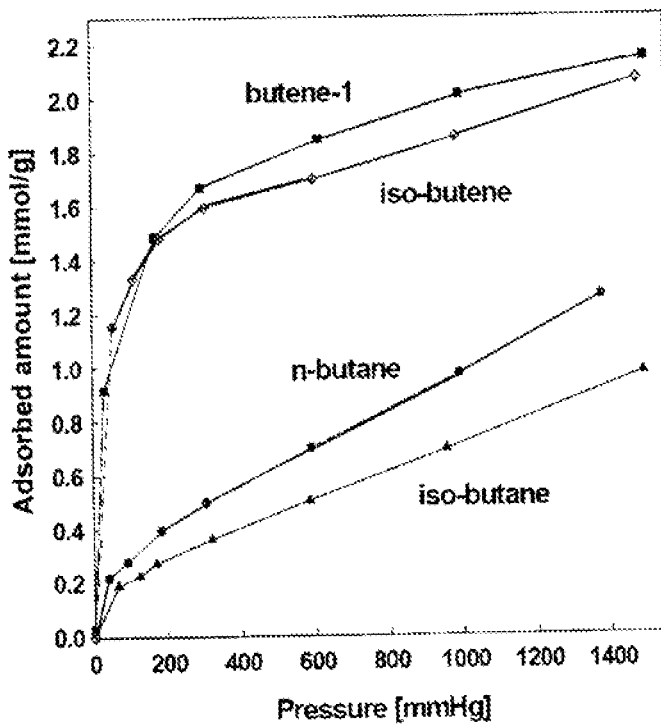
FIG. 5 is a graph of equilibrium adsorption isotherms of olefin-selective adsorbents, i.e., π-complex adsorbents.

FIG. 1 is a schematic view of the apparatus of separating C4 olefin from a mixture gas of C4 olefins/paraffins according to the present invention. The apparatus comprises three adsorption towers for separating C4 olefins via selective adsorption and two distillation towers for separating C4 olefins/desorbents and C4 paraffins/desorbents respectively. The basic process of the adsorption tower used in the present invention includes an adsorption step of selectively adsorbing C4 olefins from the gas mixture, a C4 olefin rinse step of removing a small amount of C4 paraffins adsorbed together with C4 olefins; and a C4 olefin desorption step using the desorbents and the process further can includes a pressure equalization step, a concurrent depressurization step, and a pressurization step. The desorbent discharged from the adsorption step along with olefins or paraffins is separated in the distillation tower and then recycled into the adsorption tower. The preferable desorbents is C5 hydrocarbon or C6 hydrocarbon which has a large difference in boiling point from that of the C4 mixture.

The operating method during a cycle will be explained with reference to FIG. 2 which includes all the processing step.

The mixture gas containing C4 olefins/paraffins is introduced into the adsorption tower AD-1loaded with olefin selective adsorbents through the conduit 1 and valve 1a to adsorb C4 olefins thereon (adsorption step), and the olefin free paraffin stream separated from the mixture is introduced together with the desorbents retained in the adsorption tower before the adsorption step into the distillation tower D1 through the conduit 5 and the valve 5a to separate paraffins and desorbents. The adsorption tower AD-2 carries out the step (desorption step) of desorbing olefin components with the desorbent while the adsorption tower AD-1carries out the adsorption step. The desorbents used in the desorption step is obtained from the bottoms of the distillation tower D1 and the distillation tower D2 and is introduced into adsorption tower AD-2 through the conduit 6 and the valve 6b. The olefins discharged with the desorbents is introduced into the distillation tower D2 through the valve 2a and the conduit 2 to separate the olefins and the desorbents. The adsorption tower AD-3 is provided with a portion of the olefins separated from the distillation tower D2 through the conduit 3 and the valve 3c to remove a small amount of paraffins adsorbed together with the olefins for the improvement of the purity of olefins (C4 olefin rinse step). At that time, the gas discharged from the adsorption tower AD-3 is introduced into the distillation tower D1 through the valve 4c and the conduit 4.

The adsorption tower AD-1at high pressure which just carried out the adsorption step is connected with the adsorption tower AD-2 at low pressure through the valve 4a and the conduit 4 and thus a process (pressure equalization step) that allows the pressures of both towers to be in the same pressure is carried out. During the pressure equalization step, the valve 7 is closed. The adsorption tower AD-3 alter the rinse step carries out a desorption step of recovering olefins by introducing the desorbents thereto through the conduit 6 and the valve 6c. The olefins discharged together with the desorbents from the adsorption tower AD-3 is sent to the distillation tower D2 through the valve 2c and the conduit 2 and thus separated from the desorbent.

The adsorption tower AD-1after the pressure equalization step is depressurized through the valve 4a and the conduit 4, and at that time, the discharged gas is introduced into the distillation tower D1 (concurrent depressurition step). During the concurrent depressurization of the adsorption tower AD-1, a C4 mixture gas is introduced into the adsorption tower AD-2 through the conduit 1 and the valve 1b and the adsorption tower AD-2 carries out a step (pressurization step) of increasing the pressure to the adsorption pressure. At that time, the adsorption tower AD-3 continues to carry out the desorption step.

The adsorption tower AD-1which just finished the concurrent depressurization step carry out a C4 olefin rinse step, the adsorption tower AD-2 carries out the adsorption step, and the adsorption tower AD-3 continues to carry out the desorption step.

In this way, each adsorption tower carry out a sequential adsorption step—pressure equalization step—concurrent depressurization step—C4 olefin rinse step—desorption step—pressure equalization step—pressurization step continuously.

Figure 6:
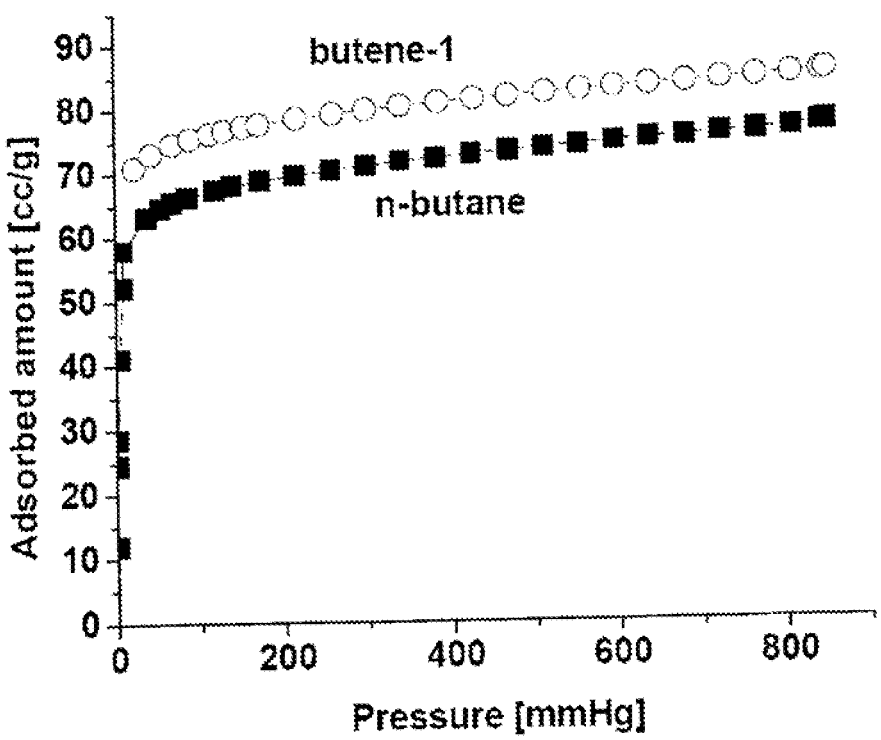
FIG. 6 is a graph of equilibrium adsorption isotherms of olefin-selective adsorbents, i.e., type 13X zeolite adsorbents.

As shown in FIG. 3 and FIG. 4, the pressure equalization step, the concurrent depressurization step or the pressurization step can be omitted from the constitution of the process depending on the processing pressure of the adsorption step FIG. 5 and FIG. 6 show the adsorption isotherms of the olefin selective adsorbents which can be loaded on the adsorption tower carrying out the method of the present invention. The adsorbents for use in the method of the present invention is π-complex adsorbent forming π-complex selectively with olefins, type X zeolite or type Y zeolite.

EXAMPLE 1

An experiment for separating olefins from a mixture gas of C4 olefins/paraffins was performed while using type 13X zeolite as an adsorbent for the separation of olefins/paraffins and using C5 mixture gas as a desorbent. The cycle sequence and the apparatus used in this example is shown in FIG. 2 and FIG. 1, respectively. The compositions of the C4 mixture gas and of the C5 mixture gas were shown in table 2. The C4 mixture gas was introduced into the adsorption process at the conditions of 60° C., 2000 mmHg and the flow rate of 1675 ml/min. The C4 olefin rinse step was carried out in the rinse flow rate of 300 ml/min.

TABLE 2

| Composition of C4 mixture gas and desorbents | |
|---|---|
| | Composition (wt %) |
| Components of mixture gas | |
| Iso-butane | 4.73 |
| Normal-butane | 15.3 |
| 1-Butene | 50.0 |
| Trans-2-butene | 19.0 |
| Cis-2-butene | 10.4 |
| Trace components | Remainder |
| Components of desorbents | |
| Normal-pentane | 80.65 |
| Iso-pentane | 18.60 |
| Cyclopentane | 0.56 |
| Trace components | 0.10 |

The performance of the process and the composition of each products resulted from the above process is shown in the following table 3.

TABLE 3

Performance of the process resulted from Example 1

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 1675 | 300 | 13 | 93.5 | 0.15 | 2.60 | 59.9 | 23.7 | 13.3 | 96.9 |

The result from the experiment carried out with the apparatus as shown in FIG. 1 while omitting the C4 olefin rinse step is shown in the following table 4.

TABLE 4

Performance of the process without the C4 olefin rinse step

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 2000 | 0 | 10 | 85.16 | 1.87 | 9.30 | 56.3 | 19.7 | 12.2 | 88.2 |

EXAMPLE 2

Table 5 is a result from the experiment conducted with cycle sequence without the pressure equalization step as shown in FIG. 3.

TABLE 5

Performance of the process of example 2

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 1610 | 300 | 13 | 93.2 | 0.14 | 2.21 | 60.6 | 23.6 | 12.9 | 97.1 |

EXAMPLE 3

Table 6 is a result from the experiment performed with the cycle sequence of adsorption step—C4 olefin rinse step—desorption step without the pressure equalization step and the concurrent depressurization step as shown in FIG. 4.

TABLE 6

Performance of the process of example 3

| Flow rate of mixture gas (ml/min) | Flow rate of C4 olefins (ml/min) | Flow rate of C5 desorbents (ml/min) | Product recovered (%) | Composition of products (wt %) | | | | | Purity of olefin |
|---|---|---|---|---|---|---|---|---|---|
| | | | | Isobutane | Normal butane | 1-Butene | Trans-2-butene | Cis-2-butene | |
| 1640 | 400 | 13 | 91.6 | 0.27 | 2.59 | 23.3 | 61.4 | 12.0 | 96.7 |

The present invention achieves an effect that the concentration of olefins in the C4 olefin product increases through the reduction of the concentration of paraffins (ex., isobutane, normal butane, etc.), by introducing a olefin rinse step into a separation process of C4 olefins (butene-1, trans-2-butene, cis-2-butene, etc.) and C4 paraffins (normal butane, isobutane, etc.) from a C4 hydrocarbon mixed gas including butene-1, trans-2-butene, cis-2-butene, normal butane, isobutane, etc.

Now, some embodiments of the present invention are illustrated with reference to the drawings accompanied. However, it is understood that the illustrated embodiments of the present invention are intended to be examples only and the invention is not limited to any embodiments.

The present invention is useful for obtaining the C4 olefins with the high purity of more than 95 wt % by introducing a C4 olefin rinse step to reduce the concentration of C4 paraffins (isobutane, normal butane, etc.) in the C4 olefin product, in the separation of C4 olefins (butene-1, trans-2-butene, cis-2-butene, etc.) and C4 paraffins (normal butene, isobutane, etc.) from a C4 hydrocarbon mixed gas including butene-1, trans-2-butene, cis-2-butene, normal butane, isobutane, etc., as proved in the Examples of the present invention.

Although the present invention has been described with respect to the exemplary embodiments in detail, these embodiments are intended only to be illustrative of the present invention and it is apparent to those skilled in the art that a variety of modifications and changes may be made without departing from the spirit and scope of the present invention.

What is claimed is:

1. An apparatus for separating C4 olefins from a mixture gas of C4 olefins/paraffins by carrying out repeated sequential adsorbing, rinsing and desorbing in such a way of performing displacement desorption using desorbents, in adsorption towers loaded with adsorbents which selectively adsorb olefins and a distillation tower for the separation olefins/desorbents and a distillation tower for the separation of paraffins/desorbents that separate the mixture gas recovered from the adsorption towers by using desorbents, wherein the adsorption tower is configured to include:

an adsorption tower (AD-1) that is connected with a feeding conduit (1) that feeds the mixture gas of C4 oleffins/paraffins, a C4 olefins/desorbents discharging conduit (2) that is connected with a distillation tower (D2), a conduit (3) that feeds a predetermined amount of C4 olefins from the distillation (D2), a conduit (4) that guides the paraffins/desorbents discharged at the rinsing to the distillation tower (D1), a conduit (5) that feeds the paraffins/desorbents discharged at the adsorbing to the distillation tower (D1), and a conduit (6) that is fed with desorbents separated from the distillation towers D1 and D2);

an adsorption tower (AD-2) that is connected with a feeding conduit (1) that feeds the mixture gas of C4 olefins/paraffins, a C4 olefins/desorbents discharging conduit (2) that is connected with a distillation tower (D2), a conduit (3) that feeds a predetermined amount of C4 olefins from the distillation (D2), a conduit (4) that guides the paraffins/desorbents discharged at the rinsing to the distillation tower (D1), a conduit (5) that feeds the paraffins/desorbents discharged at the adsorbing to the distillation tower (D1), and a conduit (6) that is fed with desorbents separated from the distillation towers (D1 and D2); and an adsorption tower (AD-3) that is connected with a feeding conduit (1) that feeds the mixture gas of C4 olefins/paraffins, a C4 olefins/desorbents discharging conduit (2) that is connected with a distillation tower (D2), a conduit (3) that feeds a predetermined amount of C4 olefins from the distillation (D2), a conduit (4) that guides the araffins/desorbents discharged at the rinsing to the distillation tower D1), a conduit(5) that feeds the paraffins/desorbents discharged at the adsorbing to the distillation tower (D1), and a conduit (6) that is fed with desorbents separated from the distillation towers (D1 and D2), and wherein the paraffins/desorbents distillation tower is the distillation tower (D1) that separates the C4 paraffins and desorbents from the adsorption towers (AD-1, AD-2, and AD-3) and the olefins/desorbents distillation tower is the distillation tower (D2) that separates the C4 olefins and desorbents from the adsorption towers (AD-1 AD-2, and AD-3).

2. The apparatus for separating C4 olefins from a mixture gas of C4 olefins/paraffins according to claim 1, further comprising a valve (7) for the conduit (4) guided to the distillation tower (D1).

3. The apparatus for separating C4 olefins from a mixture gas of C4 olefins/paraffins according to claim 1, wherein the olefin selective absorbent is selected among the π-complex adsorbent forming π-complex selectively with olefins, type X zeolite or type Y zeolite.

4. The apparatus for separating C4 olefins from a mixture gas of C4 olefins/paraffins according to claim 1, wherein the desorbent is C5 hydrocarbon or C6 hydrocarbon.

* * * * *

UNITED STATES PATENT AND TRADEMARK OFFICE
CERTIFICATE OF CORRECTION

| | | |
|---|---|---|
| PATENT NO. | : 9,034,185 B2 | Page 1 of 1 |
| APPLICATION NO. | : 13/855957 | |
| DATED | : May 19, 2015 | |
| INVENTOR(S) | : Kim et al. | |

It is certified that error appears in the above-identified patent and that said Letters Patent is hereby corrected as shown below:

On title page, item (73) Assignee: "KOREA INSTITUTE OF ENERGY RESEARCH, Daejeon (KR)" needs to be deleted and replaced with following:
(73) Assignee: KOREA INSTITUTE OF ENERGY RESEARCH, Daejeon (KR); SK ENERGY CO., LTD., Seoul (KR)

Signed and Sealed this
Eighth Day of September, 2015

Michelle K. Lee
*Director of the United States Patent and Trademark Office*